United States Patent

Schmid et al.

[11] Patent Number: 6,139,614
[45] Date of Patent: Oct. 31, 2000

[54] GONIOCHROMATIC LUSTER PIGMENTS BASED ON TITANIUM DIOXIDE-COATED SILICATIC PLATELETS WHICH HAVE BEEN HEATED IN A REDUCING ATMOSPHERE

[75] Inventors: Raimund Schmid, Neustadt; Oliver Seeger, Mannheim; Norbert Mronga, Dossenheim, all of Germany

[73] Assignee: BASF Aktiengesellschaft, Ludwigshafen, Germany

[21] Appl. No.: 09/300,451

[22] Filed: Apr. 28, 1999

[30] Foreign Application Priority Data

May 16, 1998 [DE] Germany .................. 198 22 046

[51] Int. Cl.⁷ .................................................. C09C 1/00
[52] U.S. Cl. .................... 106/417; 106/415; 106/436; 106/442; 106/482; 106/489
[58] Field of Search ...................... 106/415, 417, 106/436, 442, 482, 489

[56] References Cited

U.S. PATENT DOCUMENTS

| 3,438,796 | 4/1969 | Hanke et al. | 106/291 |
| 4,948,631 | 8/1990 | Ostertag et al. | 427/208 |
| 5,135,812 | 8/1992 | Phillips et al. | 428/403 |
| 5,607,504 | 3/1997 | Schmid et al. | 106/407 |
| 5,624,486 | 4/1997 | Schmid et al. | 106/404 |
| 5,624,487 | 4/1997 | Schmidt et al. | 106/417 |
| 5,958,125 | 9/1999 | Schmid et al. | 106/415 |

FOREIGN PATENT DOCUMENTS

| 2215215 | 3/1998 | Canada . |
| 0 753 545 | 1/1997 | European Pat. Off. . |
| 0 832 943 | 4/1998 | European Pat. Off. . |

*Primary Examiner*—C. Melissa Koslow
*Attorney, Agent, or Firm*—Oblon, Spivak, McClelland, Maier & Neustadt, P.C.

[57] ABSTRACT

Goniochromatic luster pigments are based on titanium dioxide-coated silicatic platelets which have been heated in a reducing atmosphere and which comprise at least one layer packet comprising A) a colorless coating having a refractive index $n \leq 1.8$ and B) a colorless coating having a refractive index $n \geq 2.0$.

9 Claims, No Drawings

GONIOCHROMATIC LUSTER PIGMENTS BASED ON TITANIUM DIOXIDE-COATED SILICATIC PLATELETS WHICH HAVE BEEN HEATED IN A REDUCING ATMOSPHERE

SPECIFICATION

The present invention relates to novel goniochromatic luster pigments based on titanium dioxide-coated silicatic platelets which have been heated in a reducing atmosphere and which comprise at least one layer packet comprising A) a colorless coating having a refractive index $n \leq 1.8$ and B) a colorless coating having a refractive index $n \geq 2.0$.

This invention further relates to the production of these luster pigments and to their use for coloring coatings, inks, including printing inks, plastics, glasses, ceramic products and decorative cosmetic preparations.

Luster effect pigments are used in many sectors of industry, for example in automotive coatings, decorative coating, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopiable optical effects, these pigments are increasingly gaining in importance for the production of forgeryproof security documents, such as banknotes, checks, check cards, credit cards, tax stamps, postage stamps, rail and air tickets, telephone cards, lottery tickets, gift vouchers, passes and identity cards.

Markings prepared with the luster effect pigments and the absence of these markings or their alteration, for example in a color copy (disappearance of color flops and luster effects), are reliably discernible by the unaided, naked eye and so make it easy to distinguish the copy from the original.

Particular interest pertains to goniochromatic luster pigments which exhibit an angle-dependent color change between two or more intensive interference colors and hence an attractive color play.

The prior art discloses a number of metallic-based goniochromatic luster pigments, which are produced via physical vapor deposition techniques (U.S. Pat. Nos. 3,438,796 and 5,135,812) or by coating of metal platelets by means of gas phase decomposition of volatile precursors (CVD=Chemical Vapor Deposition) or by wet-chemical coating of the metal platelets (EP-A-668 329 and EP-A-708 154).

Goniochromatic luster pigments based on transparent, silicatic substrates or coated iron(III) oxide platelets are described in DE-A-196 18 569, EP-A-753 545 and prior German Patent Application 198 08 657.1, respectively.

Prior art luster pigments differ from the pigments of the present invention in the type of substrate material and/or of the applied coatings.

It is an object of the present invention to provide further goniochromatic luster pigments which have advantageous application properties and which extend the range of coloristic opportunities.

We have found that this object is achieved by the goniochromatic luster pigments defined at the beginning.

The present invention further provides a process for producing these luster pigments, which comprises applying said coatings (A) and (B) independently of each other to said titanium dioxide-coated silicatic platelets which have been heated in a reducing atmosphere either wet-chemically by hydrolytic decomposition of organic or inorganic metal compounds or by gas phase decomposition of volatile, organic or inorganic metal compounds.

The present invention finally provides for the use of the luster pigments of the present invention for coloring coatings, inks, including printing inks, plastics, glasses, ceramic products and decorative cosmetic preparations.

The goniochromatic luster pigments of the present invention are based on titanium dioxide-coated silicatic platelets which have been heated in a reducing atmosphere and which comprise multiple coating.

Suitable silicatic platelets include especially light-colored and white micas, particular preference being given to flakes of the wet-ground muscovite. It will be appreciated that the range of useful starting materials further includes other natural micas, such as phlogopite or biotite, artificial micas, and talcum or glass flakes.

The silicatic platelets are coated with a layer which consists essentially of titanium dioxide and which may include further, preferably colorless metal oxides such as tin dioxide, zirconium dioxide, aluminum oxide and silicon dioxide as minor constituents (generally <5% by weight).

The size of the silicate platelets is not critical per se and can be adapted to the particular application intended. In general, the platelets have mean largest diameters from about 1 to 200 $\mu$m, especially from about 5 to 100 $\mu$m, and thicknesses from about 0.1 to 1 $\mu$m, especially around about 0.5 $\mu$m. Their specific free surface area (BET) is customarily within the range from 1 to 15 m$^2$/g, especially within the range from 3 to 12 m$^2$/g.

The thickness of the $TiO_2$ layer determines the reflection color of the platelets and is preferably within the range from 50 to 100 nm (silver) or within the range from 300 to 340 nm (blue; optical layer thicknesses).

To produce the luster pigments of the invention, the titanium dioxide-coated silicate platelets have been heated in a reducing gas atmosphere.

Examples of suitable reducing gases include ammonia gas, hydrogen, volatile hydrocarbons (especially $C_1$–$C_4$-alkanes) and mixtures thereof. These gases are preferably used mixed with inert gases such as nitrogen (cf. EP-A-735 115 and the references cited therein, which include EP-A-322 071).

Preferred reducing gases are ammonia gas and mixtures of ammonia gas with volatile hydrocarbons such as methane, ethane and/or propane, for which a volume ratio of from about 95:5 to 70:30 is advisable. The proportion of the particularly preferred reducing gas/inert gas mixtures which is accounted for by nitrogen is preferably, respectively, up to 90% by volume and within the range from 10 to 60% by volume.

Suitable temperatures for the reduction are preferably within the range from 750 to 850° C. when ammonia gas is used and preferably >800 to 900° C. when ammonia gas/hydrocarbon mixtures are used.

The reduction leads to the formation of blue, reduced titanium species having oxidation states <4 to 2 (lower titanium oxides such as $Ti_3O_5$, $Ti_2O_3$ to TiO, titanium oxynitrides and also titanium nitride). It is customary for from 5 to 100% by weight of the titanium dioxide originally present to be reduced.

Reduced titanium dioxide-coated mica pigments are commercially available under the name of Paliocrom®.

The reduced, titanium dioxide-coated silicatic platelets are highly refractive. Their refractive index n is generally ≧2.0, preferably ≧2.4. With regard to visible light, they vary from essentially transparent to virtually nontransparent as a function of the contemplated wavelength.

The luster pigments of the present invention combine a colorless low refractive coating (A) with a colorless high refractive coating (B). They may comprise a plurality of identical or different combinations (layer packets) of (A)+(B), but coating with just one layer packet (A)+(B) is preferred.

The colorless low refractive coating (A) has a refractive index n≦1.8, preferably ≦1.6, and an absorption constant k=0 in the visible wavelength range.

The layer material (A) is suitably any low refractive colorless substance which can be applied to the substrate platelets in the form of a durable film, inorganic materials being preferred.

Particularly suitable materials include for example metal oxides and metal oxide hydrates such as silicon oxide, silicon oxide hydrate, aluminum oxide, aluminum oxide hydrate and mixtures thereof, preference being given to silicon oxide (hydrate).

The geometric layer thickness of the coating (A) is generally within the range from 50 to 800 nm, preferably within the range from 100 to 600 nm. Since the layer (A) essentially determines the interference colors of the pigments of the present invention, it has a minimum layer thickness of about 200 nm for luster pigments which have just one layer packet (A)+(B) and which exhibit a particularly pronounced color play and hence are also preferred. If a plurality (e.g., 2, 3 or 4) of layer packets (A)+(B) are present, the layer thickness of (A) is preferably within the range from 50 to 200 nm.

As the layer thickness of (A) increases, the dry pigment powder is observed in plan view to pass repeatedly in succession through the interference colors of blue-green-gold-red-violet, the angle dependence of the hue increasing starting with the second order blue. However, the interference colors are visible only in the dry state and disappear completely in the moist state or in varnish. The additional coating with (B) renders the optically variable layer visible in varnishes, too.

The colorless high refractive coating (B) has a refractive index n≧2.0, especially ≧2.4, and an absorption constant k=0 in the visible wavelength range.

The layer material (B) is suitably any high refractive colorless substance which can be applied to the (A)-coated substrate platelets in the form of a durable film.

Particularly suitable layer materials (B) include not only metal sulfides such as zinc sulfide but especially metal oxides and metal oxide hydrates, for example titanium dioxide, titanium oxide hydrate, zirconium dioxide, zirconium oxide hydrate, tin dioxide, tin oxide hydrate, zinc oxide, zinc oxide hydrate and mixtures thereof, preference being given to titanium dioxide and titanium oxide hydrate and their mixtures with up to about 5% by weight of the other metal oxides, especially tin dioxide. Titanium dioxide can also be used together with low refractive colorless metal oxides if the refractive index of these mixtures is ≧2.0.

The coating (B) preferably has a smaller layer thickness than the coating (A). Preferred geometric layer thicknesses for coating (B) range from about 5 to 50 nm, especially from 10 to 40 nm.

The coating (B) which is preferred according to the present invention consists essentially of titanium dioxide and preferably has an optical layer thickness of ≦100 nm, i.e., is silvery by itself and does not exhibit any interference effects.

The luster pigments of the present invention are notable for high hiding power, high lightness values, intensive blue color with marked goniochromaticity and "silkily soft esthetics" in applied form and also for the uniform, homogeneous and filmlike construction of their interference-capable coating and hence add to the range of existing luster pigments in an advantageous manner.

In the process of the present invention for producing the luster pigments, the coatings (A) and (B) are applied independently of each other either wet-chemically by hydrolytic decomposition of organic or inorganic metal compounds or by gas phase decomposition (CVD) of suitable volatile metal compounds.

It will be appreciated that the two approaches may be arbitrarily combined to produce the individual layers. When both the coatings are applied wet-chemically there is no need for the (A)-coated substrate platelets to undergo intermediary drying; if the same reaction medium is used, intermediary isolation may likewise be dispensed with. Accordingly, intermediary isolation is customarily not necessary either when both the coating steps are carried out according to the CVD process.

The wet-chemical production route and the CVD production route are equally suitable for preparing the silicon and/or aluminum oxide (hydrate) layers (A).

The wet-chemical variant may advantageously be conducted in accordance with the process described in EP-A-668 329, which comprises hydrolyzing organic silicon and/or aluminum compounds in which the organic radicals are attached to the metals via oxygen atoms in the presence of the substrate platelets and of an organic solvent in which the metal compounds are soluble and which is miscible with water.

The preferred embodiment comprises hydrolyzing the metal alkoxides (especially tetraethoxysilane and aluminum triisopropoxide) in the presence of an alcohol (especially isopropanol or ethanol) and of aqueous ammonia as catalyst.

The process described in EP-A-668 329 is preferably carried out by providing substrate platelets, isopropanol, water and ammonia as initial charge, heating this mixture to 40–80° C., especially 60–70° C., with stirring, and continuously adding a solution of the metal alkoxide in isopropanol by metering. Following a post-addition stirring time of usually from about 1 to 15 h, the mixture is cooled down to room temperature, and the coated pigment is isolated by filtration and drying.

Silicon oxide (hydrate) coatings (A) may advantageously also be produced from alkali metal silicates, especially sodium silicate.

An advantageous procedure is to suspend the substrate platelets in water, heat the suspension to about 20–100° C., preferably 40–80° C., using a base (especially an alkali metal hydroxide solution such as potassium hydroxide solution or sodium hydroxide solution) to set a pH of generally 4–9, preferably 6.5–8.5, especially about 7.5, and meter in the alkali metal silicate solution while at the same time adding an aqueous inorganic acid such as hydrochloric acid, especially dilute hydrochloric acid, to keep the pH constant. If necessary, the batch is subsequently stirred for a period ranging from a few min up to 2 h.

The CVD variant may be carried out according to the process described in EP-A-708 154. Silanes containing at least one alkanoyloxy radical are decomposed in the gas phase using water vapor and, if the silanes also contain alkyl or phenyl radicals, oxygen in the presence of the fluidized substrate platelets.

Preferred silanes have alkoxy and alkanoyloxy radicals, and particular preference is given to di-tert-butoxydiacetoxysilane.

To carry out the CVD variant it is advisable to employ (as generally customary for CVD processes) a fluidized bed reactor. The substrate platelets are fluidized in the reactor with an inert gas such as nitrogen while being heated to the desired reaction temperature (generally 100–600° C., preferably 150–300° C.), and then silane and water vapor (and also, if appropriate, oxygen) are then introduced via separate nozzles from upstream vaporizer vessels with the aid of inert carrier gas streams (advantageously bleed streams of the fluidizing gas), the silane concentration being advantageously maintained at $\geq 5\%$ by volume, preferably $\leq 2\%$ by volume, based on the total amount of gas in the reactor. The amount of water vapor should be not less than the amount stoichiometrically required to hydrolyze the silane, but from 10 to 100 times that amount is preferable.

Similarly, the coatings (B) may be deposited both by the CVD route and by the wet-chemical route.

Suitable starting compounds for the CVD variant include especially metal alkoxides, metal halides and organometals. Preference is given to compounds which have a sufficiently high vapor pressure at temperatures below 200° C. to ensure simple vaporization, ideally without decomposition.

Suitable alkoxides include aromatic alkoxides such as phenoxides and benzyl alkoxides and also aliphatic, especially $C_1$–$C_4$, alkoxides such as n-, iso- and tert-butoxides, preferably methoxides and ethoxides and especially n- and iso-propoxides and also mixtures thereof.

The metal halides are preferably chlorides.

Organometals may be for example metal alkyls, especially those having up to 4 carbon atoms in the alkyl chain, metal alkenyls, metal aryls, metal arylalkyls and metal alkylalkenyls.

Examples of suitable starting compounds are:

alkoxides such as titanium tetraethoxide, titanium tetra-n-propoxide and titanium tetraisopropoxide and especially mixtures of titanium tetraethoxide and titanium tetraisopropoxide, preferably in a molar ratio of about 1:1, which are notable for low vaporization temperatures (around 120° C.) and also low decomposition temperatures (hydrolysis with water vapor possible at about 200° C.), and also zirconium n- and iso-propoxide;

halides such as titanium tetrachloride, zirconium tetrachloride and tin tetrachloride;

organics such as tin tetramethyl, tin tetra-n-butyl and zinc diethyl.

The decomposition of these metal compounds to form metal oxide layers which form filmlike deposits on the (A)-coated substrate platelets is advantageously likewise effected in a fluidized bed reactor, using water vapor and optionally air in the case of the alkoxides, water vapor in the case of the halides and oxygen as additional reaction gas in the case of the organics. Suitable decomposition temperatures range generally from 100 to 600° C., preferably from 150 to 300° C. (alkoxides), from 150 to 350° C. (halides) and from 300 to 500° C. (organics).

Similarly to the metal oxide (hydrate) coatings (A), the metal oxide (hydrate) layers (B) may likewise be applied wet-chemically by hydrolysis of metal alkoxides (titanium ethoxide, for example) in an alcoholic medium or preferably by hydrolysis of inorganic metal salts, especially halides, preferably chlorides, in aqueous suspension.

In an advantageous embodiment for depositing the preferred titanium dioxide layers (B), an aqueous suspension of the (A)-coated substrate platelets is heated to customarily 50–100° C., preferably 70–80° C., adjusted to a pH which is generally within the range from 0.5 to 5, preferably within the range from 1.5 to 2.5, especially about 2.2, with a base (especially an alkali metal hydroxide solution such as potassium hydroxide solution or sodium hydroxide solution), and a titanium tetrachloride solution is metered in at the same time as a base is added to keep the pH constant.

The deposited titanium oxide (hydrate), whether deposited from the gas phase or wet-chemically, is only incompletely crystalline. The amorphous portions can be converted into a crystalline form, customarily into the anatase form, by calcining the isolated (and dried) pigment. For this, the pigment is generally heated to 400–1000° C. for about 1–4 h. If the titanium dioxide coating (B) is to be in the rutile form after calcination, it is advisable to dope the titanium oxide (hydrate) with about 0.5–10% by weight of tin dioxide by simultaneous deposition of tin oxide (hydrate) to favor the formation of the rutile form.

The production process of the present invention makes it possible to produce the multiply coated luster pigments reproducibly in a simple manner in large volumes. The pigment particles obtained are completely enrobed and the individual coatings are of high quality (homogeneous, filmlike).

The luster pigments of the present invention are very useful for many purposes, such as coloring plastics, glasses, ceramic products, decorative cosmetic preparations and especially coatings and inks, including printing inks, including security printing inks. All industrially customary printing processes are suitable, for example screen printing, intaglio printing, bronze printing, flexographic printing and offset printing.

For these applications, the pigments of the present invention are also advantageously usable in admixture with transparent and hiding white, color and black pigments and also conventional luster pigments based on metal oxide-coated mica and metal pigments and known goniochromatic luster pigments.

EXAMPLES

Production and Use of Luster Pigments According to the Invention

To evaluate the coloristics of the pigments obtained, in each case 0.4 g of the pigment was stirred into 3.6 g of a polyester mixing varnish having a solids content of 21% by weight and dispersed in a Red Devil® for 2 min. A draw bar (wet film thickness 200 $\mu$m) was then used to prepare single-stroke drawdowns of the pigmented varnishes on a piece of black and white cardboard. After the film had dried, the CIELAB values were measured with a Multiflash goniospectrophotometer from Optronik at an angle difference of from 20° to 115° to the specular angle against a black background. The reported color coordinates relate to the standard illuminant D65. L is the lightness, a* is the red/green content and b* is the blue/yellow content. H is the hue angle and C is chroma. This measuring set-up will capture only part of the color play, namely essentially the color of the coating in plan view.

Inventive Example a) 100 g of a blue-silvery, ammonia-reduced $TiO_2$ mica pigment (Paliocrom® Blausilber L6000, BASF) were slurried up in 1.5 l of isopropanol and admixed initially with 400 g of water and 40 g of 25% strength by weight aqueous ammonia solution and, after heating to 60° C., with a mixture of 345 g of tetraethoxysilane and 345 g of isopropanol, this mixture being added over about 24 h. Following a post-addition stirring time of about 2 h and cooling down of the suspension, the product was filtered off, washed with isopropanol and dried at 80° C. under reduced pressure.

The dried SiO$_2$-coated pigment (203 g) had a masstone color which was violet in air and invisible in varnish.

b) A suspension of 100 g of the SiO$_2$-coated and dried product in 1350 ml of water was heated to 75° C. and then adjusted to pH 2.2 with 32% strength by weight hydrochloric acid. Thereafter 120 ml of an aqueous titanium tetrachloride solution (200 g of TiCl$_4$/l) were added over 120 min. The pH was maintained at a constant 2.2 by the simultaneous addition of 32% strength by weight sodium hydroxide solution. Following a post-addition stirring time of 30 min and cooling down of the suspension, the product was filtered off, washed with water and dried at 80° C. under reduced pressure.

The pigment obtained had a silicon content of 26.1% by weight and a titanium content of 12.9% by weight. Applied in varnish, the pigment exhibited high hiding power and an angle-dependent color play from intensively greenish blue to violet at a high lightness level.

Colorimetric data of pigment obtained:

| Measuring angle in ° | L | a* | b* | C | H |
| --- | --- | --- | --- | --- | --- |
| 20 | 74.2 | −11.1 | −35.7 | 37.4 | 252.7 |
| 25 | 69.9 | −12.1 | −30.2 | 32.5 | 248.2 |
| 35 | 49.6 | −11.1 | −21.5 | 24.2 | 242.7 |
| 45 | 39.5 | −8.5 | −17.2 | 19.2 | 243.7 |
| 55 | 33.2 | −6.2 | −15.1 | 16.3 | 247.7 |
| 65 | 28.3 | −4.1 | −13.5 | 14.1 | 253.3 |
| 75 | 37.3 | −3.7 | −13.2 | 13.7 | 254.4 |
| 115 | 24.1 | −1.9 | −13.1 | 13.2 | 262.0 |

Comparative Example

For comparison, the colorimetric data of the SiO$_2$— and molybdenum-coated mica pigment Paliocrom® Blausilber L6000 of Example 4 of EP-A-753 545 were determined.

This pigment had a titanium content of 7.7% by weight, a silicon content of 29.6% by weight and a molybdenum content of 2.6% by weight. Applied in varnish, this pigment likewise exhibited high hiding power, but only an angle-dependent color play from greenish blue to violet at low color strength and at a considerably lower lightness level.

Colorimetric data of pigment obtained:

| Measuring angle in ° | L | a* | b* | C | H |
| --- | --- | --- | --- | --- | --- |
| 20 | 58.2 | −8.8 | −22.3 | 23.9 | 248.5 |
| 25 | 48.7 | −9.1 | −18.6 | 20.7 | 244.0 |
| 35 | 33.3 | −8.2 | −12.3 | 14.8 | 236.1 |
| 45 | 23.0 | −6.6 | −8.4 | 10.7 | 231.7 |
| 55 | 16.4 | −4.9 | −6.4 | 8.1 | 232.3 |
| 65 | 11.5 | −3.0 | −5.4 | 6.1 | 241.0 |
| 75 | 10.6 | −2.6 | −5.1 | 5.7 | 242.9 |
| 115 | 7.2 | −0.8 | −3.9 | 4.0 | 259.0 |

We claim:

1. Goniochromatic luster pigments based on titanium dioxide-coated silicatic platelets which have been heated in a reducing atmosphere and which comprise at least one layer packet comprising A) a colorless coating having a refractive index n≦1.8 and B) a colorless coating having a refractive index n≧2.0, adjacent to A.

2. Luster pigments as claimed in claim 1, wherein said coating (B) has an optical layer thickness of ≦100 nm.

3. Luster pigments as claimed in claim 1, wherein said coating (A) consists essentially of silicon oxide, silicon oxide hydrate, aluminum oxide and/or aluminum oxide hydrate.

4. Luster pigments as claimed in claim 1, wherein said coating (B) consists essentially of titanium dioxide, titanium oxide hydrate, zirconium dioxide, zirconium oxide hydrate, tin dioxide, tin oxide hydrate, zinc oxide, zinc oxide hydrate and/or zinc sulfide.

5. Luster pigments as claimed in claim 1, comprising just one said layer packet.

6. Luster pigments as claimed in claim 1, wherefor the titanium dioxide-coated silicatic platelets have been heated in a reducing atmosphere comprising ammonia gas, hydrogen or volatile hydrocarbons or mixtures thereof.

7. Luster pigments as claimed in claim 1, wherefor the titanium dioxide-coated silicatic platelets have been heated in a reducing atmosphere comprising ammonia gas or a mixture of ammonia gas and volatile hydrocarbons.

8. A process for producing luster pigments as claimed in claim 1, which comprises applying said coatings (A) and (B) independently of each other to said titanium dioxide-coated silicatic platelets which have been heated in a reducing atmosphere either wet-chemically by hydrolytic decomposition of organic or inorganic metal compounds or by gas phase decomposition of volatile, organic or inorganic metal compounds.

9. A process for coloring coatings, inks, plastics, glasses, ceramic products or decorative cosmetic preparations, which comprises incorporating the luster pigments of claim 1 into these coatings, inks, plastics, glasses, ceramic products or decorative cosmetic preparations.

* * * * *